(12) United States Patent
Dalmia et al.

(10) Patent No.: US 6,571,650 B2
(45) Date of Patent: Jun. 3, 2003

(54) VARIABLE HEADSPACE SAMPLING SYSTEM

(75) Inventors: Avinash Dalmia, Danbury, CT (US); Otto J. Prohaska, Danbury, CT (US); Paul G. Saviano, Norwalk, CT (US); Gitesh Kumar, Norwalk, CT (US)

(73) Assignee: PerkinElmer Instruments LLC, Shelton, CT (US)

( * ) Notice: Subject to any disclaimer, the term of this patent is extended or adjusted under 35 U.S.C. 154(b) by 0 days.

(21) Appl. No.: 10/029,668

(22) Filed: Oct. 22, 2001

(65) Prior Publication Data

US 2003/0074987 A1 Apr. 24, 2003

(51) Int. Cl.⁷ .................................................. G01N 1/12
(52) U.S. Cl. ...................................... 73/864; 73/864.62
(58) Field of Search ............................. 73/864.62, 864, 73/40, 40.7, 49.8, 23.34

(56) References Cited

U.S. PATENT DOCUMENTS

| | | | |
|---|---|---|---|
| 2,413,261 A | | 12/1946 | Stackhouse |
| 2,647,399 A | * | 8/1953 | Newbill, Jr. .................... 73/88 |
| 3,499,326 A | * | 3/1970 | Matier et al. ............... 73/421.5 |
| 3,902,851 A | | 9/1975 | Dravnieks |
| 4,096,734 A | | 6/1978 | Khayat |
| 4,145,915 A | * | 3/1979 | Oertle et al. .................... 73/37 |
| 4,563,893 A | | 1/1986 | Tanyolac et al. |
| 4,770,027 A | | 9/1988 | Ehara et al. |
| 4,884,435 A | | 12/1989 | Ehara |
| 5,052,906 A | * | 10/1991 | Seemann ..................... 425/112 |
| 5,178,021 A | * | 1/1993 | Kosuth ..................... 73/864.62 |
| 5,404,747 A | * | 4/1995 | Johnston et al. ............... 73/40 |
| 5,522,253 A | | 6/1996 | Knight |
| 5,753,285 A | | 5/1998 | Horan |
| 5,965,803 A | | 10/1999 | Chinn, Jr. et al. |
| 6,018,984 A | * | 2/2000 | McGinley et al. ......... 73/23.34 |
| 6,085,576 A | | 7/2000 | Sunshine et al. |

* cited by examiner

*Primary Examiner*—Helen Kwok
*Assistant Examiner*—C D Garber
(74) *Attorney, Agent, or Firm*—St. Onge Steward Johnston & Reens LLC

(57) ABSTRACT

The invention relates to an apparatus and method for providing a modifiable headspace for measuring a concentration of volatile releases from a sample. The invention includes a collapsible housing for containing the air sample and a plurality of spacers between the housing and the sample surface for separating them from one another. The plurality of spacers permit the distance between the housing and the sample to be adjustable.

19 Claims, 3 Drawing Sheets

VARIABLE HEADSPACE SAMPLING SYSTEM

FIELD OF THE INVENTION

The invention relates to a sampling system for monitoring volatile releases and, more particularly, a system that provides for a modifiable headspace used for measuring a concentration of volatiles emanating from a surface.

BACKGROUND OF THE INVENTION

Measuring odors and bacteria plays an important role in the field of quality inspection, for example, when the freshness of perishable foods being shipped is to be evaluated. Other examples include control of fermentation and classification by grade of food, such as seaweed, coffee, alcoholic beverages or the like in accordance with volatile concentrations. For such quality inspections, it is generally important to measure individual volatiles as well as the total concentration of volatiles. Volatiles are airborne releases from a surface that indicate a level of spoilage and/or contamination. They are known to have an odor or be odorless. Multiple surfaces have volatile releases. Besides food surfaces, waste, perishables, and non-perishables alike emit volatiles.

Conventionally, the above-mentioned quality inspections have been carried out by odor organoleptic tests. For example, by human sense of smell. Such inspections are typically possible for those who have a keen sense of smell and taste and are well trained to perform such inspections. However, such training is generally time consuming. Further, the results of the inspections may differ depending upon the physical conditions of the inspector. Moreover, odorless volatiles would be undetected.

Devices for collecting air samples from a food's surface for measuring concentrations of volatiles were developed to overcome the disadvantages of the human nose. These devices typically require the air samples to reach equilibrium, or have a consistent concentration of volatiles throughout the samples, in order to provide accurate and reproducible measurements. In order to reach equilibrium, one may wait a sufficient amount of time for the volatile releases to self disperse evenly throughout an air sample. Therefore, the response time for an air sample to be collected is typically dependent upon the size of the sample.

Known devices for collecting air samples typically include rigid containers and flexible bags. Overall, rigid containers were found to provide reproducible results because the headspace, the clearance between the surface of the sample and container was advantageously fixed. However, smaller samples of food generally had slow response times due to a large headspace whereas larger samples had quick response times. Hence, the containers did not provide consistent response times among varying samples.

Flexible bags overcame the disadvantage of rigid containers in that they generally captured air samples of varying volumes around odd-shaped samples quicker because the headspace may be advantageously adjusted to each sample size. Such odd-shaped samples of foods include chicken legs, fish fillets, ribs, and the like. However, bags do not have structural integrity and collapse and sometimes stick to the surfaces they are covering, thereby further reducing the air samples to those sample surfaces that are not stuck to a collapsed bag. Because the bag may stick to the sample in unpredictable and asymmetric locations, a larger, localized headspace may require a longer time to reach equilibrium than a smaller headspace on the same piece of sample. This disadvantageously affects reproducibility and results in inconsistent response times.

What is desired, therefore, is a device that minimizes air samples for measuring volatile releases from variably sized surfaces. What is also desired is a device having structural integrity and providing an adjustable headspace. What is further desired is a device for providing reproducible measurements of volatiles.

SUMMARY OF THE INVENTION

Accordingly, it is an object of the invention to provide an adjustable housing for covering a surface of a sample.

It is another object of the invention to provide a housing that minimizes the headspace over the sample in order to provide an air sample of volatiles having the desired concentration of volatile releases in a shorter period of time.

It is a further object of the invention to provide a housing having at least one device for adjusting the headspace.

It is still another object of the invention to provide a housing for covering a localized area of the sample surface.

These and other objects of the invention are carried out by an apparatus having a modifiable headspace for measuring a concentration of volatile releases from a sample surface. The apparatus includes a collapsible housing for containing the air sample and a plurality of spacers between the housing and sample surface for separating them from one another. The plurality of spacers further provides an adjustable distance between the housing and the sample.

The plurality of spacers may be attached one at a time or, if clustered together in tandem or groups, attached several at a time. This permits optimum flexibility because one may adjust the distance between the housing and sample at any location on the sample surface. This adjustment is not readily available when the spacers are integrally formed with the housing at predetermined locations.

The apparatus further includes an outlet for permitting the air sample to be extracted from the housing and an inlet for permitting air to enter the housing, thereby facilitating the extraction.

To determine the quantity of volatile releases present in the headspace, a sensor or other handheld instrument for testing may be connected to the outlet.

The housing may be flexible and have no structural integrity, thereby requiring the plurality of spacers to prevent the housing from collapsing onto the sample surface. The housing may further be a flexible bag made of a leak proof material to prevent volatile releases from escaping.

In another embodiment, the plurality of spacers is integrally formed with the collapsible housing. This facilitates the application of the spacers because by merely covering the sample surface with the housing, the spacers are simultaneously applied as well.

In another embodiment, the housing covers the sample surface in a localized area as opposed to covering the entire surface. This embodiment is particularly useful where the sample cannot fit within the housing or when localized testing of the sample surface is desired. The housing for covering a localized area of sample may be a funnel or container.

In another embodiment, an air sampling kit is provided further including a tray. The tray is for holding and handling the sample and for further transporting the kit from one location to another.

In another aspect of the invention, a method for measuring a concentration of volatile releases is provided. The method includes covering a sample with a housing, attaching a plurality spacers to the sample for separating the housing from the surface, adjusting the headspace or volume of air between the sample and housing, and extracting an air sample for testing.

The invention and its particular features and advantages will become more apparent from the following detailed description considered with reference to the accompanying drawings.

DETAILED DESCRIPTION OF THE DRAWINGS

Figure 1:
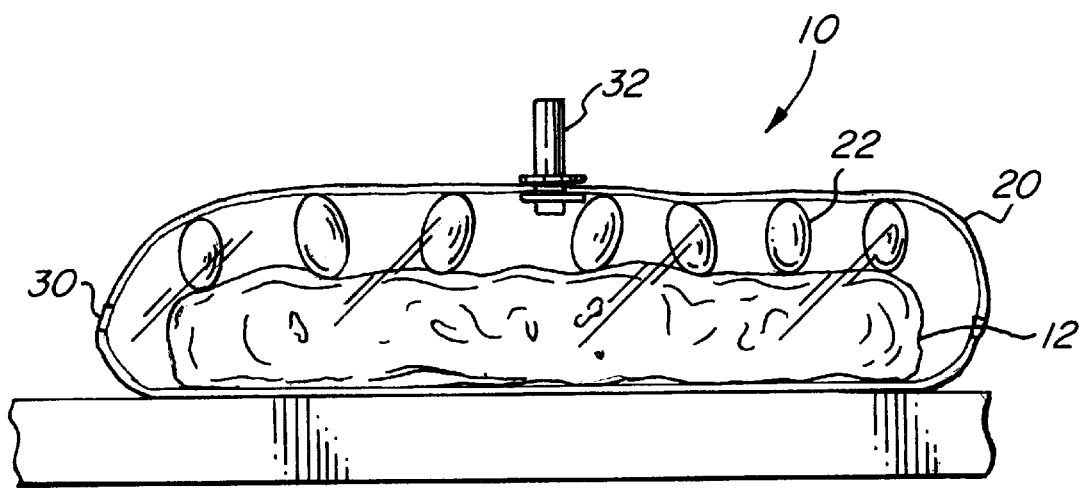
FIG. 1 depicts the variable headspace sampling system in accordance with the invention.

FIG. 1 depicts the variable headspace sampling system 10 in accordance with the invention. System 10 includes housing 20 for covering a sample 12, plurality of spacers 22 for separating housing 20 from sample 12, housing inlet 30 for permitting a flow of air into housing 20, and housing outlet 32 for permitting a flow of vapor to be tested.

Sample 12 is any article capable of giving off, or emitting, volatile releases. For example, food, wastes, perishables, and non-perishables alike emit volatile releases. Other examples include clothing, soil, water and shoes. Further, volatile releases are known to be odorless as well as having an odor. Where sample 12 gives off volatile releases is not germane to the invention, although volatiles are usually released from a surface of sample 12.

System 10 operates to facilitate the detection of food spoilage and/or detecting volatile concentrations by providing a sample of air immediately surrounding sample 12 for testing. Spoiled food emits volatiles/odors generated by bacteria, whereby these volatile releases are most abundant in the air immediately adjacent to the food sample. Therefore, system 10 operates to contain a sample of air, including the volatile releases, immediately adjacent to food sample 12 for testing. Known or novel testing devices, such as handheld instruments using electrochemical sensors, surface acoustic wave devices, electronic nose type devices, or gas chromatographs are used to test the sample of air obtained by system 10. These testing devices test the contained air sample by drawing air from outlet 32.

The volume of air contained between housing 20 and sample 12 is defined to be the headspace. The headspace further contains the volatile releases. The concentration of volatile releases is directly related to both the size of the headspace and the amount of time that has elapsed after sample 12 has begun to emit volatiles into the headspace. The longer the period of time, the more volatiles are released and the greater the concentration. Also, the longer one waits, the more homogeneous the concentration of volatile releases in the headspace, thereby providing more reproducible and accurate results. The desired concentration of volatiles in the headspace varies depending on the testing device used. Therefore, to reduce the amount of time required to obtain the requisite volatile concentration, the headspace should be minimized since volatiles are emitted from sample 12 at a nonadjustable rate.

Housing 20 is used to gather and contain a sample of air immediately adjacent to sample 12. The air sample contained includes the volatile releases. Housing 20 is also sufficiently air tight, meaning the sample of air gathered and contained should not leak or escape through pores or seals in housing 20 or that only a negligible amount is lost or escapes. Hence, sufficiently air tight is defined to be a loss of no more than 5% of the total volume of sample gas contained by housing 20 in a given time period. Suitable materials include known or novel air tight materials, such as plastic. In addition, the material used should not absorb a sufficient volume of the odor or volatile releases because absorption would, like leakage from a non air tight material, distort the measurement results. A nonporous material is not required for system 10 to function properly but no more than 5% of the total volume of sample gas contained by housing 20 should be absorbed in a given time period. The required thickness of housing 20 is only so that housing 20 has sufficient structural integrity to resist breakage when being handled. Furthermore, housing 20 should be made of a flexible material so that the headspace may be desirably minimized/adjusted, such as a bag.

Although it is desired to minimize the headspace, the headspace should not be minimized to the point where housing 20 touches sample 12 for touching a wide area of the sample surface effectively reduces the volume of the air sample to a non-measurable amount. Touching further compartmentalizes the air sample into multiple, smaller volumes of air samples. This is undesirable because food, for example, may spoil in certain localized areas of the surface and the concentration of volatiles may vary among the compartmentalized volumes. A test of a compartmentalized volume may falsely indicate that the food sample has not spoiled when, in fact, another compartmentalized volume contains unsafe levels of bacteria, which would have been detected but for the closed off compartmentalized headspace.

Plurality of spacers 22 is used to separate housing 20 from sample 12. Plurality of spacers 22 may be made of a material the same or similar to housing 20. However, similar materials are not required for proper functioning of system 10. Furthermore, unlike housing 20, plurality of spacers 22 does not have a requirement for preventing odor absorption or air leakage. Hence, any known or novel materials may be used for spacers 22 so long as it has sufficient structural integrity to prevent housing 20 from coming in contact with the sample 12. Therefore, spacers 22 are generally more brittle or have less flexibility than housing 20. In fact, housing 20 is to be flexible and structural integrity is not required for maintaining a form or shape, but is required for preventing breakage. On the other hand, spacers 22 should have sufficient structural integrity to maintain a shape or form in order to prevent housing 20 from sagging and collapsing upon the sample 12. Spacers 22 may further be hollow or solid. Spacers 22 include a plurality of balloons, toothpicks, or any known or novel objects for providing a distance between housing 20 and sample 12.

Spacers 22 may further be placed on sample 12 prior to covering sample 12 with housing 20. Spacers 22 need not be attached to housing 20 for system 10 to operate. In this manner, spacers 22 may be strategically placed on the sample surface so as to prevent housing 20 from touching sample 12 when applied. For example, spacers 22 may be more concentrated in an area of sample 12 that has crevices and less concentrated in areas of sample 12 having raised regions. This manner may be time consuming if the spacers are applied one at a time over a large sample 12. Therefore, spacers 22 may be combined in tandem or in a cluster with one another at predetermined distances such that one may apply multiple spacers at one time.

Figure 4:
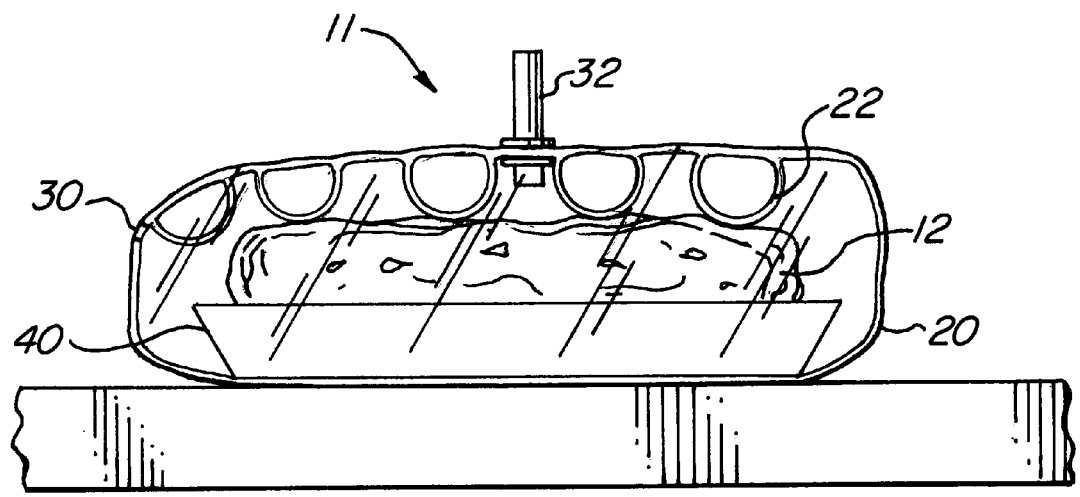
FIG. 4 depicts the variable headspace sampling system having integrally formed spacers for separating the housing from the sample.

In another embodiment and to further facilitate applying the spacers, plurality of spacers 22 are formed integrally with housing 20, as depicted in FIG. 4. In this manner, one simultaneously covers sample 12 with housing 20 and applies spacers 22 at the same time.

Referring again to FIG. 2, housing outlet 32 permits air sample within the headspace to be extracted from housing 20 for testing by a testing device. The air sample is extracted from the headspace by known or novel manners, such as vacuum, suction, pressure differences, or other forms of extracting vapor.

As the air sample is being extracted from outlet 32, air from outside housing 20 should enter inlet 30 in order to facilitate the extraction of air sample from outlet 32. Without inlet 30 or air from outside housing 20 entering the headspace, pressure decreases within housing 20. As pressure decreases, the more difficult it is to extract the air sample from outlet 32 and the greater the possibility of housing 20 collapsing onto the sample. Inlet 30 is not necessary for the air sample to be extracted from outlet 32 but inlet 30 greatly facilitates the extraction for pressure inside housing 20 is in equilibrium with the air pressure outside housing 20. Moreover, in certain embodiments, multiple inlets and outlets are used to further facilitate and expedite air sample extraction, thereby providing uniform distribution of air and increased testing reproducibility. Multiple inlets and outlets are particularly useful for large housings.

Inlet 30 and outlet 32 may further be combined to form a single unit. The outlet and inlet are maintained as separate channels having air flow in only one direction each but the inlet and outlet are in contact with one another, thereby requiring only one aperture in housing 20. In an alternative embodiment, the inlet and outlet are combined into a single unit having a single channel that has air flow in two directions. This requires air to be extracted from a channel and, upon removing the instrument for extracting the air sample, permits air to enter housing 20 through the same channel. This embodiment is less efficient than having two separate channels because as the amount of volume being extracted increases, the greater the pressure difference may be between the headspace and surrounding air, thereby making extraction more difficult. However, it is this pressure difference that causes air to enter the housing upon removing the instrument for extraction.

Figure 2:
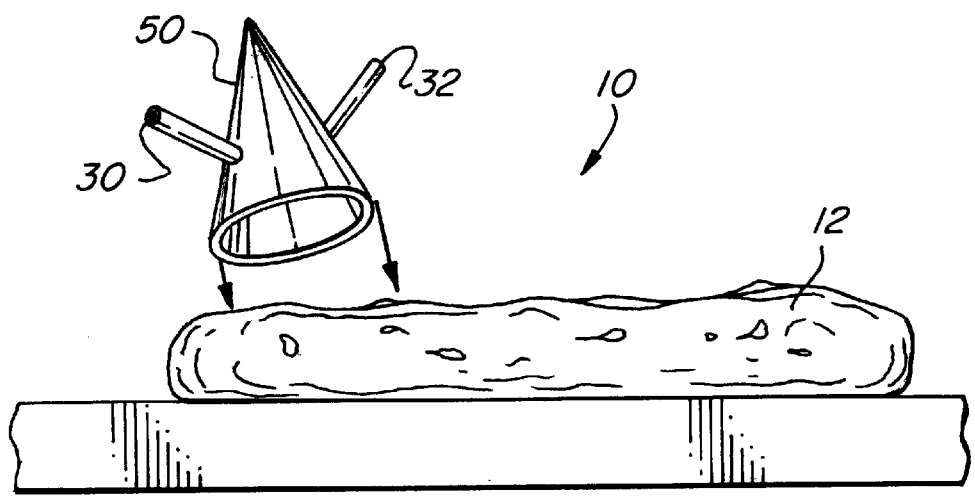
FIG. 2 depicts a system for providing an air sample of a localized surface area of the sample.

In another embodiment, FIG. 2 depicts the sampling system 10 having overlay 50 instead of housing 20 for covering a localized surface of sample 12. System 10 includes overlay 50, inlet 30 for permitting a flow of air into overlay 50, and outlet 32 for permitting an air sample to be tested.

System 10 operates to facilitate the detection of volatiles in a localized area by providing a sample of air immediately surrounding the area of concern. For example, food may spoil in selected areas of food sample 12 and sampling the entire food surface is not necessary. Furthermore, the food sample to be tested may be larger than the above described housing 20 under FIG. 1, such as an entire pig, cow, watermelon, head of lettuce, or any food sample that cannot fit inside housing 20. When sample 12 cannot fit inside housing 20, housing 20 becomes inoperable for purposes of providing an air sample having a concentration of volatile releases. However, overlay 50 is ideal in such situations.

As depicted, overlay 50 is a funnel that is sufficiently rigid so that it does not collapse onto sample 12. Sufficiently rigid is defined to mean a material that retains memory of shape. The material may be flexible when subjected to force, but should return to its original shape when the force is removed and provided the force does not cause plastic deformation. However, overlay 50 is not required to be sufficiently rigid and, in certain embodiments, it is made of a collapsible material, such as the flexible material used for housing 20 above described under FIG. 1. If a collapsible material is used, plurality of spacers 22 may be used with overlay 50 for separating overlay 50 from sample 12.

When overlay 50 is made of a rigid material, such as plastic, metal, or other nonmalleable material, overlay 50 is self supporting and does not require plurality of spacers 22 for preventing overlay 50 from touching sample 12. Overlay 50 is a handheld device for covering sample 12 and should be sized accordingly. As such, it should not be cumbersome to handle. Because the headspace is not adjustable when using overlay 50, system 10 includes numerous overlays 50 of varying sizes to accommodate varying sizes of localized areas for testing. Therefore, a user may pick from a selection of different sized overlays when covering a selected area.

Figure 3:
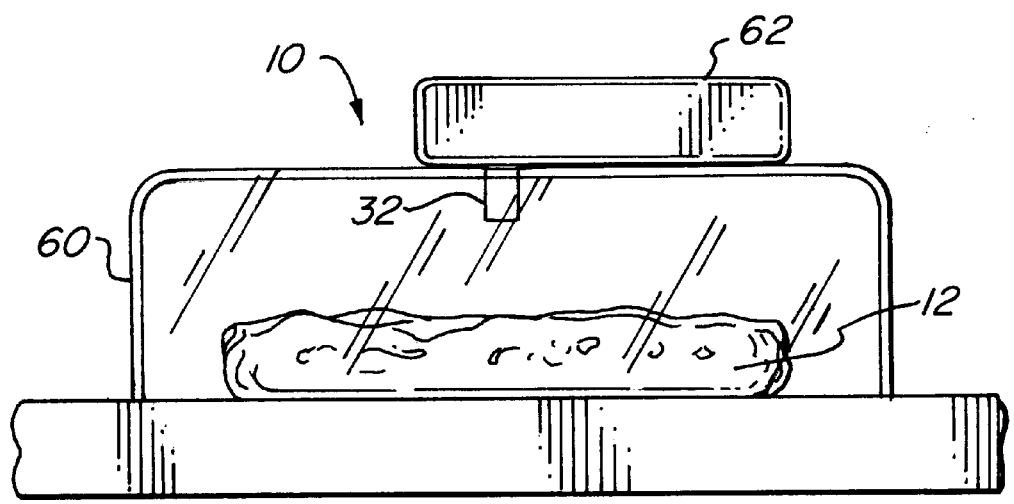
FIG. 3 depicts a system for providing an air sample of an entire surface area of the sample.

FIG. 3 depicts another embodiment of system 10, whereby housing 20 is a rigid covering. System 10 includes all the limitations described above under FIG. 1, including housing inlet 30 for permitting a flow of air into housing 20 and housing outlet 32 for permitting a flow of sample gas to be tested.

Housing 20 is to be made of a sufficiently rigid material. Because housing 20 is a rigid covering, system 10 need not include plurality of spacers 22 for housing 20 is self supporting. In other words, housing 20 has sufficient structural integrity such that it does not collapse or touch food 12.

Because the headspace is not adjustable when housing 20 is a rigid covering, system 10 includes numerous housings 50 of varying sizes to accommodate varying sizes of samples 12 for testing. Therefore, a user may pick from a selection of different sized housings when covering sample 12. Housing 20 is used to completely cover sample 12 and provide an air sample for testing by a known or novel testing device 62. Device 62 includes handheld instruments and/or gas chromatographs in connection with and drawing the air sample from outlet 32.

FIG. 4 depicts an air sampling kit 11 providing an adjustable headspace, including housing 20 for covering a sample 12, plurality of spacers 22 for separating housing 20 from sample 12, housing inlet 30 for permitting a flow of air into housing 20, housing outlet 32 for permitting a flow of vapor to be tested, and tray 40 for holding sample 12. Kit 11 is a complete system for providing a sample of air for testing for food spoilage.

Housing 20 includes plurality of spacers 22 integrally formed with housing 20. In this manner, one simultaneously covers sample 12 with housing 20 and applies spacers 22 at the same time. This embodiment facilitates application of the spacers and, in this respect, improves upon the embodiment described in FIG. 1. Plurality of spacers 22 repeatedly places housing 20 over sample 12 at approximately the same distance from the surface of sample 12, regardless of the shape of sample 12 because the separation plurality of spacers 22 provides is fixed. Hence, sampling kit 11 provides improved repeatability. The embodiment includes bubble wrap as a possible material for housing 20 with integrally formed spacers 22.

Tray 40 includes known or novel materials for holding sample 12, including plastic, metal, wood, fiberglass, ceramic, glass, or any material rigid and strong enough to hold a sample 12. Tray 40 should not be collapsible or malleable for it would make sample handling difficult. Tray 40 operates to facilitate sample handling, such as carrying samples from one location to another. Tray 40 also permits kit 11 to be carried from one area to another for a user may simultaneously handle tray 40 through housing 20 and carry kit 11, including sample 12, as one unit. Tray 40 may further include a handle or lip on the edge of tray 40 to further facilitate sample handling. Tray 40 should fit completely within housing 20 and preferably should be free from sharp corners to prevent tearing housing 20.

Figure 5:
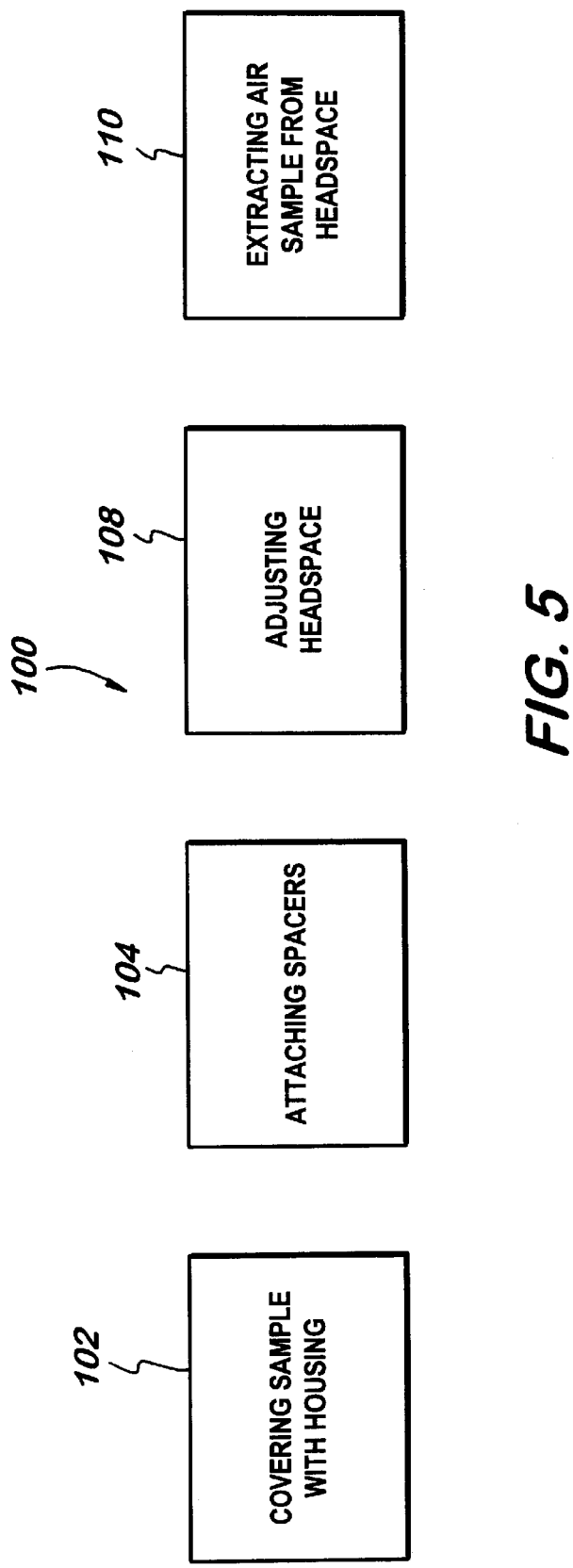
FIG. 5 depicts a method for measuring a concentration of volatile releases from a sample surface.

FIG. 5 depicts method 100 for measuring a concentration of volatile releases from a sample surface. The method includes covering 102 a sample with a housing, attaching 104 a plurality spacers to the sample for separating the housing from the sample, adjusting 108 the headspace or volume of air between the sample and housing, and extracting 110 an air sample for testing.

Covering 102 a sample includes using a housing that either completely or partially covers the sample. Sample size, desired response time of the test, and desired degree of repeatability all affect the choice of housing. The housing may be flexible, as depicted in FIGS. 14, or rigid, as depicted in FIG. 3. Flexibility permits headspace adjustment. Rigid housings permit quick application. The housing may also be for covering a localized area, as depicted in FIG. 2, or for use in an air quality sampling kit, as depicted in FIG. 4. The housing may further include integrally formed spacers for separating the housing from the sample.

Attaching 104 a plurality of spacers to the sample includes strategically placing the spacers in areas requiring more and/or less support for the subsequent placement of the housing. Attaching 104 the spacers also includes placing the spacers one at a time or in clusters. Instead of attaching spacers to the sample, one m,ay attach the spacers to the housing. Moreover, the spacers may be integrally attached to the housing, as depicted in FIG. 4.

Adjusting 108 the headspace includes modifying the distance between the sample surface and housing. Desirably, the volume of air contained within the housing is to be minimized to reduce response time while providing a sufficient concentration of volatile releases. Adjusting 108 the headspace includes moving at least one spacer into the sample, such as placing the spacer further within the sample surface. Adjusting 108 the headspace also includes moving the spacer along the sample surface to areas lower in elevation. Moreover, adjusting 108 includes reducing the size of the spacers, selectively removing spacers, or any other way of modifying the volume of air between the housing and sample.

Extracting 110 an air sample for testing includes vacuuming, suctioning, or pressurizing the headspace so that the air sample can be removed from the housing for testing. Method 100 includes any known or novel manners of extracting the air sample.

Although the invention has been described with reference to a particular arrangements of parts, features and the like, these are not intended to exhaust all possible arrangements or features, and indeed many other modifications and variations will be ascertainable to those of skill in the art.

What is claimed is:

1. An apparatus having a modifiable headspace for measuring a concentration of volatiles from a sample emitting volatiles, comprising:
   a collapsible housing for covering a surface of a sample; and
   a plurality of spacers between said housing and said surface for separating said housing from said surface by a variable distance to adjust the headspace.

2. The apparatus according to claim 1, wherein said plurality of spacers are formed integrally with said collapsible housing.

3. The apparatus according to claim 1, wherein said plurality of spacers are attached to the surface of the sample before the surface of the sample is covered by said collapsible housing.

4. The apparatus according to claim 1, wherein said plurality of spacers are attached to the sample surface before the sample is covered by said collapsible housing.

5. The apparatus according to claim 1, wherein said housing further includes an inlet for permitting air to enter said housing and an outlet for permitting gas to be extracted from said housing.

6. The apparatus according to claim 5, wherein said inlet and said outlet are combined.

7. The apparatus according to claim 5, wherein said outlet is connected to a sensor.

8. The apparatus according to claim 5, wherein said outlet is connected to a hand-held instrument.

9. The apparatus according to claim 8, wherein said hand-held instrument is a gas chromatograph.

10. The apparatus according to claim 1, wherein said housing is a flexible material.

11. The apparatus according to claim 10, wherein said housing is a flexible bag.

12. The apparatus according to claim 1, wherein said housing is leak proof.

13. A method for measuring a concentration of volatile releases from a sample, comprising:
   covering a surface of the sample with a collapsible housing to measure a concentration of volatiles from the surface;
   providing a plurality of spacers for separating the collapsible housing from the surface; and
   adjusting a plurality of spacers between the collapsible housing and the surface to modify a distance of separation.

14. The method according to claim 13, further comprising the step of using a select number of spacers from the plurality of spacers for varying a distance between the collapsible housing and the surface.

15. The method according to claim 13, further comprising the step of permitting air to enter the housing.

16. The method according to claim 13, further comprising the step of extracting gas from the housing.

17. The method according to claim 13, further comprising the step of connecting the collapsible housing to a sensor.

18. The method according to claim 13, further comprising the step of integrally forming the plurality of spacers with the collapsible housing.

19. A method for measuring a concentration of volatile releases from a sample, comprising:
   attaching a plurality of spacers to a surface of the sample for separating a collapsible housing from the surface;
   adjusting the plurality of spacers to modify a distance of separation between the collapsible housing and the surface; and
   covering the surface of the sample with the collapsible housing to measure a concentration of volatiles.

* * * * *